United States Patent [19]

Rao et al.

[11] Patent Number: 4,637,901

[45] Date of Patent: Jan. 20, 1987

[54] N-(ALPHA-HALOACYL)-N-HYDROCARBYL CARBAMOYL HALIDES

[75] Inventors: Chennupati K. Rao, Bhopal; Sudershan K. Arora, Hatam Tai; Raman Grover, Bhopal, all of India; John A. Durden, Raleigh; Themistocles D. J. D'Silva, Chapel Hill, both of N.C.

[73] Assignee: Union Carbide Corporation, Danbury, Conn.

[21] Appl. No.: 786,721

[22] Filed: Oct. 15, 1985

Related U.S. Application Data

[63] Continuation of Ser. No. 743,277, Jun. 11, 1985, abandoned, which is a continuation of Ser. No. 533,725, Sep. 19, 1983, abandoned.

[51] Int. Cl.$^4$ ............................................. C07C 125/03
[52] U.S. Cl. .................................................. 260/544 C
[58] Field of Search ..................................... 260/544 C

[56] References Cited

U.S. PATENT DOCUMENTS 3,152,175  10/1964  Ottenheym et al. ............. 260/544 C
3,197,503  7/1965  Smith et al. ...................... 260/544 C

FOREIGN PATENT DOCUMENTS 1226450  3/1971  United Kingdom .

*Primary Examiner*—Natalie Trousof
*Assistant Examiner*—L. Hendriksen
*Attorney, Agent, or Firm*—Gerald L. Coon

[57] ABSTRACT

Novel N-(alpha-haloacyl)-N-hydrocarbyl carbamoyl halides and a process for their preparation are provided. The novel compounds are useful as intermediates in the preparation of insecticides.

14 Claims, No Drawings

N-(ALPHA-HALOACYL)-N-HYDROCARBYL CARBAMOYL HALIDES

This application is a continuation of prior U.S. application Ser. No. 743,277, filed June 11, 1985, and which is a continuation of application Ser. No. 533,725, filed Sept. 19, 1983.

FIELD OF INVENTION

This invention relates in general to novel N-(alpha-haloacyl)-N-hydrocarbylcarbamoyl halides and to a process for their preparation. In one aspect, this invention relates to novel carbamoyl halides which are useful as intermediates in the preparation of pesticides.

BACKGROUND OF THE INVENTION

Prior to the present invention few literature references were available which disclosed carbamoyl halides. For example, British Pat. No. 1,226,450 which was published Mar. 31, 1971 disclosed certain N-substituted N-acylcarbamic acid halides of the formula:

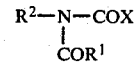

wherein R' represents alkyl, aralkyl, alkenyl aralkenyl, cycloalkyl, heterocyclic or aryl radicals, $R^2$ represents alkyl or alkynyl radicals and X represents halogen. The reference further indicates that $R^1$ and $R^2$ may be optionally substituted with certain other groups. However, compounds wherein $R^1$ is an alpha-haloalkyl were not disclosed.

British patent specification No. 1,232,930, published May 26, 1971 discloses compounds of the formula:

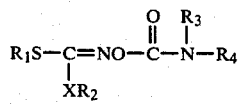

wherein $R_3$ represents a hydrogen atom or alkyl, and $R_4$ represents an optionally substituted alkanoyl group particularly, acetyl, chloroacetyl, dichloroacetyl and trichloroacetyl.

Accordingly, one or more objects will be achieved by the practice of the present invention. It is an object of this invention to provide novel carbamoyl halides. Another object of this invention is to provide novel N-(alpha-haloacyl)-N-hydrocarbylcarbamoyl halides. A further object of this invention is to provide carbamoyl halides such as N-chloroacetyl-N-methylcarbamoyl chloride, N-chloroacetyl-N-propylcarbamoyl chloride, N-alpha-chloropropionyl-N-methylcarbamoyl chloride, N-bromoacetyl-N-methylcarbamoyl chloride, N-chloroacetyl-N-methylcarbamoyl fluoride, and the like. A still further object of this invention is to provide processes for the preparation of the novel carbamoyl halides. Another object is to provide carbamoyl halides which are useful for the preparation of alpha-haloacyl carbamates of oximes, phenols and alcohols and alpha-haloacyl ureas from amines. These and other objects will readily become apparent to those skilled in the art in the light of the teachings herein set forth.

SUMMARY OF THE INVENTION

In its broad aspect the invention relates to novel N-(alpha-haloacyl)-N-hydrocarbylcarbamoyl halides, processes for their preparation and use of the compounds as intermediates for the preparation of pesticides. The novel carbamoyl halides can be represented by the following formula I:

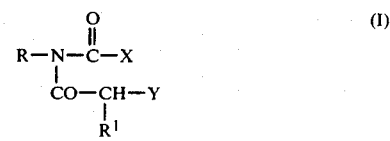

wherein R, $R^1$, X and Y are as hereinafter described.

DETAILED DESCRIPTION OF THE INVENTION

As indicated above, the novel carbamoyl halides of this invention are conveniently represented by the formula:

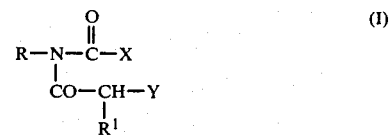

wherein:

R represents alkyl, alkenyl, alkynyl, cycloalkyl, cycloalkenyl, aralkyl, of up to 18 carbon atoms, and wherein such groups may be optionally substituted with halogen, cyano, nitro or alkoxy, alkylthio, alkyl, alkenyl, alkynyl or cycloalkyl groups of up to 12 carbon atoms;

$R^1$ represents hydrogen, halo, or alkyl. $R^1$ preferably contains up to 18 carbon atoms and can optionally be substituted with halogen, cyano, nitro or alkoxyl, alkylthio, alkenyl, alkynyl or cycloalkyl groups of up to 12 carbon atoms. X represents Cl or F and Y represents Cl, F or Br.

Illustrative novel carbamoyl halides which are encompassed by the aforementioned formula are illustrated by, but not limited to, the following: N-Chloroacetyl-N-ethylcarbamoyl chloride, N-(n-Butyl)-N-chloroacetylcarbamoyl chloride, N-Chloroacetyl-N-(n-pentyl)carbamoyl chloride, N-Chloroacetyl-N-(n-hexyl)carbamoyl chloride, N-Chloroacetyl-N-isopropylcarbamoyl chloride, N-Chloroacetyl-N-isobutylcarbamoyl chloride, N-Chloroacetyl-N-isoamylcarbamoyl chloride, N-Chloroacetyl-N-(2-propen-1-yl)carbamoyl chloride, N-Chloroacetyl-N-(2-propyn-1-yl)carbamoyl chloride, N-Chloroacetyl-N-(2-cyanoethyl)carbamoyl chloride, N-Chloroacetyl-N-(2-chloroethyl)carbamoyl chloride, N-Chloroacetyl-N-(2-methoxyethyl)carbamoyl chloride, N-Chloroacetyl-N-(2-methylthioethyl)carbamoyl chloride. N-Chloroacetyl-N-cyanomethyl carbamoyl chloride, N-Chloroacetyl-N-cyclopropyl carbamoyl chloride, N-Chloroacetyl-N-cyclohexylcarbamoyl chloride, N-Chloroacetyl-N-propyl carbamoyl fluoride, N-bromoacetyl-N-butyl carbamoyl fluoride, N-(2-Chlorobutyryl)-N-methylcarbamoyl fluoride, N-(2-Chlorohexanoyl)-N-methylcarbamoyl chloride, N-(2-fluoropropionyl)-N-methylcarbamoyl chloride, and the like.

The novel carbamoyl halides of this invention are conveniently prepared by the reaction of alpha-haloacyl chlorides with suitable isocyanates according to the scheme set forth below:

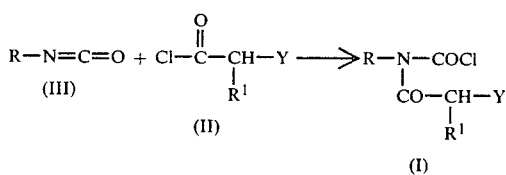

wherein R, $R^1$ and Y are as previously indicated.

Freshly activated zinc chloride supported on silica gel is the preferred catalyst for this reaction. Freshly activated zinc chloride in combination with other supports such as clay, sand, anhydrous magnesium sulfate are also effective catalysts. However, various other Lewis acid catalysts such as $SnCl_4$, $SnCl_3$, CuCl, CuBr, $HgCl_2$, $ZnBr_2$, $SbCl_5$, $TiCl_4$, etc. may also be used in a suitably activated form or in combination with inert supporting materials or heterogeneous reaction catalyzing materials such as crown ethers and quaternary ammonium salts.

Suitable reaction temperatures fall in the range from $-30°$ to $+150°$ C., however, temperatures from $0°$ to $75°$ C. are preferred. The reaction can be carried out in absence of a solvent, however inert solvents such as hydrocarbons, chlorinated hydrocarbons, ethers, nitriles, sulfones and ketones may be used. The reaction can be carried out under atmospheric pressure but lower or higher pressures may also be used.

Using reagent grade anhydrous zinc chloride catalyst, as used to prepare the prior art (Brit. Pat. Sp. No. 1226450) compounds, chloroacetyl chloride and methyl isocyanate do not afford the desired product, whereas γ-chlorobutyryl chloride smoothly reacts with methyl isocyanate to yield the corresponding N-(γ-chlorobutyryl)-N-methylcarbamoyl chloride.

The novel carbamoyl fluorides of this invention are conveniently prepared from the corresponding carbamoyl chlorides (I) by an exchange reaction. For example, N-chloroacetyl-N-methylcarbamoyl fluoride is prepared from N-chloroacetyl-N-methylcarbamoyl chloride by reacting the chloride with anhydrous potassium fluoride as indicated in Example 6. Other metal fluorides, such as the alkali and alkaline earth fluorides can also be used to effect the exchange. For example sodium fluoride or cesium fluoride can equally as well be employed.

As hereinbefore indicated the novel compounds of this invention are useful as intermediates in the preparation of pesticides and other related compounds. It has been observed that the N-(alpha-haloacyl)-N-hydrocarbylcarbamoyl halides of the present invention differ markedly in the reactivity from the prior art compounds disclosed in the aforementioned British patent specification No. 1,226,450. This is believed to be due in part to the unique alpha-position of the halogen atom as opposed to the beta- or gamma halo position of the known compounds. In addition to the highly reactive carbamoyl halide function, the halogen of the alpha-haloacyl function is thus sufficiently reactive so that it can be subsequently substituted by various nucleophiles. For example, the compounds of this invention react with phenols and oximes to yield the corresponding N-(alpha-haloacyl)-N-hydrocarbyl carbamates. These carbamates can be further reacted with various nucleophiles to yield pesticidally or otherwise biologically active derivatives.

For example, the reaction of a novel carbamoyl halide of this invention affords the corresponding N-haloacylcarbamate in high yield:

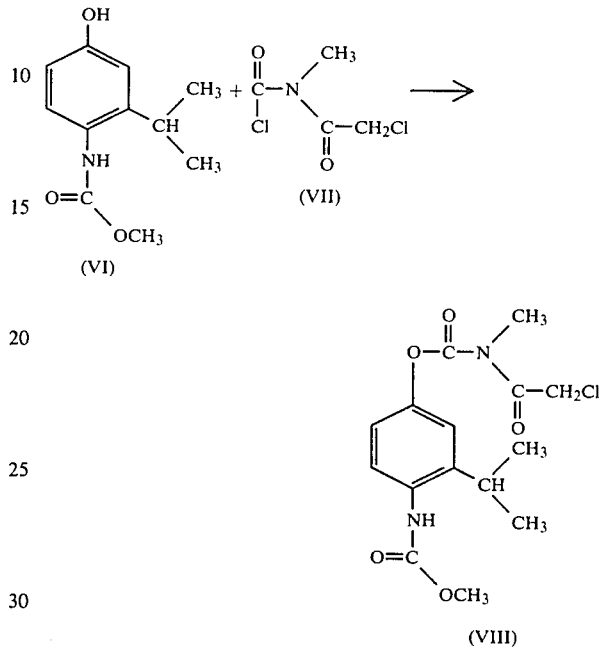

Further reaction of the carbamate with trimethyl amine gives the corresponding amine salt which has excellent pesticidal properties:

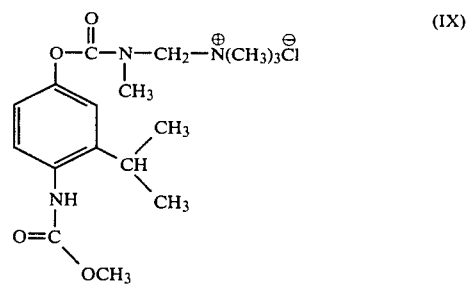

Similarly, the carbamoyl halide can be reacted with an oxime in accordance with the following equation:

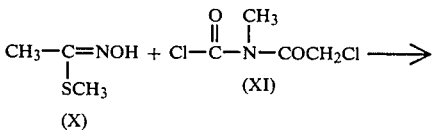

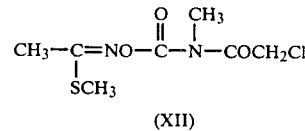

In contrast, it was noted that a similar reaction of the prior art (Brit. Pat. Sp. No. 1,226,450) compounds (XIII) with (X) lead to less active or inactive materials (XIVa) and (XIVb) as set forth in Table I.

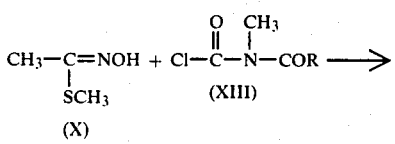

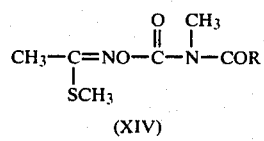

The following examples illustrate the best mode presently contemplated for the practice of this invention.

EXAMPLE 1

Preparation of Representative Catalysts Suitable for the Preparation of N-(alpha-haloacyl)-N-hydrocarbylcarbamoyl halides Catalyst A: 10 g of reagent grade anhydrous zinc chloride and 10 g. of silica gel were ground together to give an intimate mixture. This mixture was heated in an open beaker in a furnace at about 350° C. for about 1 hour to activate and spread the zinc chloride uniformly over the surface of the silica gel particles. The material was then cooled in a desiccator and directly used for the reaction. Zinc chloride and silica gel may be used in various other proportions, however, a minimum proportion of silica gel which can prevent the formation of lumps of the catalyst is preferred.

Catalyst B: 10 g. of silica gel was treated with a solution of 10 g of anhydrous zinc chloride in 25 c.c. distilled water. Water was stripped off under reduced pressure at about 80° C. The resultant powder was then heated in an open beaker in a furnace at 350° C. for about 1 hour, cooled in a desiccator and directly used for the reaction.

Catalyst C: Reagent grade anhydrous zinc chloride was fused in an open beaker on flame or in a furnace at about 350° C. The fused liquid was spread out over a smooth surface like a watch glass or a tin lid and cooled in a desiccator over fused calcium chloride. After cooling, the zinc chloride was scraped off and the flakes were ground to a fine powder under dry nitrogen.

Catalyst D: Reagent grade anhydrous zinc chloride was fused and cooled as in the case of catalyst C. Silica gel was also activated at 350° C. and cooled similarly. Equal quantities of the activated zinc chloride and silica gel were ground together to fine powder. The ratios of zinc chloride and silica gel may be varied from 0.1 percent to 80 percent of zinc chloride mixed with silica gel.

EXAMPLE 2

Preparation of N-Chloroacetyl-N-methylcarbamoyl chloride

A mixture of 20.0 g. of Catalyst A and 56.5 g. (0.50 m) of chloroacetyl chloride was stirred under dry nitrogen. Cooling the reaction flask in an ice bath, 31.5 g (0.55 m) of methyl isocyanate was added. Stirring was continued and the bath temperature was raised slowly to 50° C. under reflux. The reaction was continued at 50°–55° C. for about 16 hours and then cooled to room temperature. The unreacted chloroacetyl chloride and methyl isocyanate were stripped off at room temperature under 0.25 mm pressure. The residual solid was extracted with dichloromethane and then the solvent was stripped off under reduced pressure to afford 60.0 g (yield 70.5%) of N-Chloroacetyl-N-methylcarbamoyl chloride. M.p. 67°–69° C.

NMR (CDCl$_3$) δ4.65 (s, 2H) and 3.50 (s, 3H); I.R. (CHCl$_3$) υ1765 and 1740 cm$^{-1}$; Calcd for C$_4$H$_5$Cl$_2$NO$_2$: C, 28.26; H, 2.96; N, 8.24; Found: C, 28.40; H, 2.97; N, 8.12.

The above reaction when carried out in a closed reactor under autogeneous pressure at 0° C. to 30° C. and worked up similarly, gave the product in 80.5% yield.

Use of 11.0 g. of the Catalyst C or 22.0 g. of the Catalyst D in the above reaction and purification of the product by sublimation or distillation under reduced pressure resulted in each case in about 53 percent yield of the product.

EXAMPLE 3

Preparation of N-Chloroacetyl-N-propylcarbamoyl chloride n-Propyl isocyanate was reacted with chloracetyl chloride in presence of Catalyst A, similar to Example 2, to afford N-chloroacetyl-N-(n-propyl)-carbamoyl chloride in 78% yield. M.p. 40°–44° C.

NMR (CDCl$_3$) δ4.65 (s, 2H), 3.90 (t, 2H), 1.70 (m, 2H) 0.90 (t, 3H); IR (CDCl$_3$) υ1755 & 1735 cm$^{-1}$.

EXAMPLE 4

Preparation of N-(α-Chloropropionyl)-N-methylcarbamoyl chloride

A mixture of 2.0 g. of the Catalyst C and 28.2 g. (0.25 m) of α-Chloropropionyl chloride was stirred under nitrogen at 0° C. and 14.5 g. (0.25 m) of methylisocyanate was added dropwise. The mixture was stirred at room temperature for 16 hours and then refluxed for about 12 hours, Cooled to room temperature and the liquid was decanted from the solid catalyst. Unreacted methyl isocyanate and α-chloropropionyl chloride were stripped off under reduced pressure. The residual product was purified by distillation at 69°–76° C. under about 0.4–0.5 mm pressure to afford 8.5 g. (23%) of the title compound (a low melting solid).

NMR (CCl$_4$) δ5.25 (q, 1H), 3.40 (s, 3H) and 1.65 (d, 3H); IR (Neat) υ1770 and 1735 cm$^{-1}$

EXAMPLE 5

Preparation of N-Bromoacetyl-N-methylcarbamoyl chloride

A mixture of 5.0 g. of the Catalyst C and 30.0 g (0.19 m) of bromoacetyl chloride was stirred at 0° C. under nitrogen and 13.0 g (0.23 m) of methyl isocyanate was added dropwise. Stirring was continued and the temperature was slowly raised to 50° C. under reflux during 5 hours. The reaction was almost complete and the mixture was solidified. The product was purified by distillation under reduced pressure to afford 23.0 g (yield 56.0%) of N-bromoacetyl-N-methylcarbamoyl chloride.

B.p. 90°–95° C./3–5 mm; NMR (CCl$_4$) δ4.50 (s, 2H) and 3.50 (s, 3H); IR (CHCl$_3$) υ1750 and 1730 cm$^{-1}$.

EXAMPLE 6

Preparation of N-Chloroacetyl-N-methylcarbamoyl fluoride

A mixture of 10.0 g of N-Chloroacetyl-N-methylcarbamoyl chloride, 3.8 g of anhydrous potassium fluoride and 0.5 g of 18-crown-6 in 50 cc of dichloromethane was stirred at room temperature under nitrogen for about 16 hours. The liquid was decanted and the residue was extracted with 50 cc dichlormethane. The dichloromethane layers were combined and the solvent stripped off to afford 9.0 g. (Yield 100%) of N-chloroacetyl-N-methylcarbamoyl fluoride. The product was further purified by distillation under reduced pressure. B.p. 59° C./0.2 mm.

NMR(CDCl$_3$) δ4.70(s, 2H) and 3.30(d,3H, J 2 Hz); 1R (CHCl$_3$) υ1820 and 1735 cm$^{-1}$.

A comparision of an oxime derivative of the novel compounds of this invention was evaluated to determine its pesticidal activity against certain mites and insects including the Bean Aphid, Southern Army Worm, Mexican Bean Beetle and house fly. The oxime derivative was also compared with typical derivative of this oxime as disclosed in British Pat. No. 1,226,450.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound.

Certain of the test compounds were also prepared by dissolving 375 mg of compound in 7.5 ml of dimethylformamide. Fifteen ml of acetone containing 37.5 mg (10 percent of the weight of test compound) of an alkylphenoxy polyethoxyethanol surfactant, as a wetting-/emulsifying/dispersing agent was added to the dimethylformamide solution. Fifty-two and a half ml of water was mixed into the dimethylformamide-acetone mixture to give roughly 75 ml of a suspension containing the compound in solution or in finely divided form. The thus prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae Scop.*) reared on potted dwarf nasturtium plants at 68°-70° F. and 50±5 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids were placed on a revolving turntable and sprayed with 100-110 milliliters of test compound formulation by use of a DeVilbiss spray gun set at 40 psig air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°-70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (*Cram.*)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for five days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis, Muls.*), reared on Tendergreen bean plants at a temperature of 80°±5° F. and 50±5 percent relative humidity, were the test insects.

For certain of the tests second instar larvae (weighing about 6 mg) of the Mexican bean beetle (*Epilachna varvestis, Muls*), reared on Seiva Pole lima bean plants at a temperature of 80°±5° F. and 5±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters or test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica, L.*), reared according to the specifications of the Chemical Specialties Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80°±5° F. and a relative humidity of 50±5 percent. Flies which showed no sign of movement on prodding were considered dead.

The biological comparison of the compounds are set forth in Table I below where the insecticidal superiority of materials produced from compositions of this invention relative to previously disclosed materials is clearly demonstrated.

TABLE I

Comparison of Known Compounds With Alpha-haloacyl Compounds

| Compound | Biological activity ($LD_{50}$ in ppm) | | | |
|---|---|---|---|---|
| | Bean Aphid | Southern Army Worm | Mexican Bean Beetle | House Fly |
| (XII) | 16 | 20 | 35 | 6 |
| (XIVa) R = CH$_2$CH$_2$CH$_2$Cl | 37 | 310 | 310 | 25 |
| (XIVb) R = C$_2$H$_5$ | 500 | 60 | 200 | 500 |

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. Carbamoyl halide compounds of the formula:

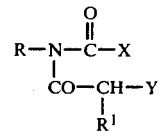

wherein:
R represents methyl or alkenyl, alkynyl, cycloalkyl, cycloalkenyl, of up to 18 carbon atoms; $R^1$ represents hydrogen or methyl; and X represents Cl or F and Y represents Cl, F or Br.

2. The compounds of claim 1 wherein X and Y represent chloro groups.

3. The compounds of claim 1 wherein X represents chloro and Y represents bromo.

4. The compounds of claim 1 wherein X represents fluoro and Y represents the chloro group.

5. The compounds of claim 1 wherein R represents methyl and $R^1$ represents hydrogen.

6. The compounds of claim 1 wherein R represents alkenyl and $R^1$ represents hydrogen.

7. The compounds of claim 1 wherein R represents alkynyl and $R^1$ represents hydrogen.

8. The compounds of claim 1 wherein R represents cycloalkyl and $R^1$ represents hydrogen.

9. The compounds of claim 1 wherein R represents cycloalkenyl and $R^1$ represents hydrogen.

10. The compounds of claim 1 wherein R and $R^1$ represent methyl.

11. The compounds of claim 1 which is N-chloroacetyl-N-methylcarbamoyl chloride.

12. The compounds of claim 1 which is N-(alpha-chloro-propionyl)-N-methylcarbamoyl chloride.

13. The compounds of claim 1 which is N-bromoacetyl-N-methylcarbamoyl chloride.

14. The compounds of claim 1 which is N-chloroacetyl-N-methylcarbamoyl fluoride.

* * * * *